United States Patent
Zeyss et al.

(10) Patent No.: US 6,852,877 B1
(45) Date of Patent: Feb. 8, 2005

(54) PROCESS FOR THE PRODUCTION OF VINYL ACETATE

(75) Inventors: Sabine Zeyss, Königstein (DE); Uwe Dingerdissen, Seeheim-Jugenheim (DE); John Fritch, Corpus Christi, TX (US)

(73) Assignee: Celanese International Corp., Dallas, TX (US)

( * ) Notice: Subject to any disclaimer, the term of this patent is extended or adjusted under 35 U.S.C. 154(b) by 0 days.

(21) Appl. No.: 10/258,956

(22) PCT Filed: May 19, 2000

(86) PCT No.: PCT/EP00/04545

§ 371 (c)(1),
(2), (4) Date: Nov. 19, 2002

(87) PCT Pub. No.: WO01/90043

PCT Pub. Date: Nov. 29, 2001

(51) Int. Cl.[7] ............................................. C07C 67/00
(52) U.S. Cl. ..................... 560/241; 560/243; 560/245
(58) Field of Search ................................ 560/231, 241, 560/129

(56) References Cited

U.S. PATENT DOCUMENTS

| | | |
|---|---|---|
| 3,972,954 A | 8/1976 | Bertus |
| 6,040,474 A * | 3/2000 | Jobson et al. ................ 560/243 |
| 6,399,816 B1 * | 6/2002 | Borchert et al. .......... 562/512.2 |
| 6,417,422 B1 * | 7/2002 | Liu ............................. 585/658 |

FOREIGN PATENT DOCUMENTS

| | | |
|---|---|---|
| DE | 19745902 | 4/1999 |
| WO | 9805620 | 2/1998 |
| WO | wo 99/20592a * | 4/1999 |

* cited by examiner

*Primary Examiner*—Johann Richter
*Assistant Examiner*—Karl Puttlitz
(74) *Attorney, Agent, or Firm*—Muserlian, Lucas and Mercanti

(57) ABSTRACT

A process for the production of vinyl acetate comprising contacting in a first reaction zone a gaseous feedstock comprising essentially ethane with a molecular oxygen-containing gas in the presence of a catalyst to produce a first product stream comprising acetic acid; contacting in a second reaction zone a gaseous feedstock comprising essentially ethane with a molecular oxygen-containing gas in the product stream comprising ethylene; contacting in a third reaction one the first gaseous product stream and the second gaseous product stream with a molecular oxygen-containing gas in the presence of a catalyst to produce a fourth product stream comprising vinyl acetate; separating the product stream from step (3) and recovering vinyl acetate from said product stream from step (3).

7 Claims, 1 Drawing Sheet

PROCESS FOR THE PRODUCTION OF VINYL ACETATE

Figure 1:
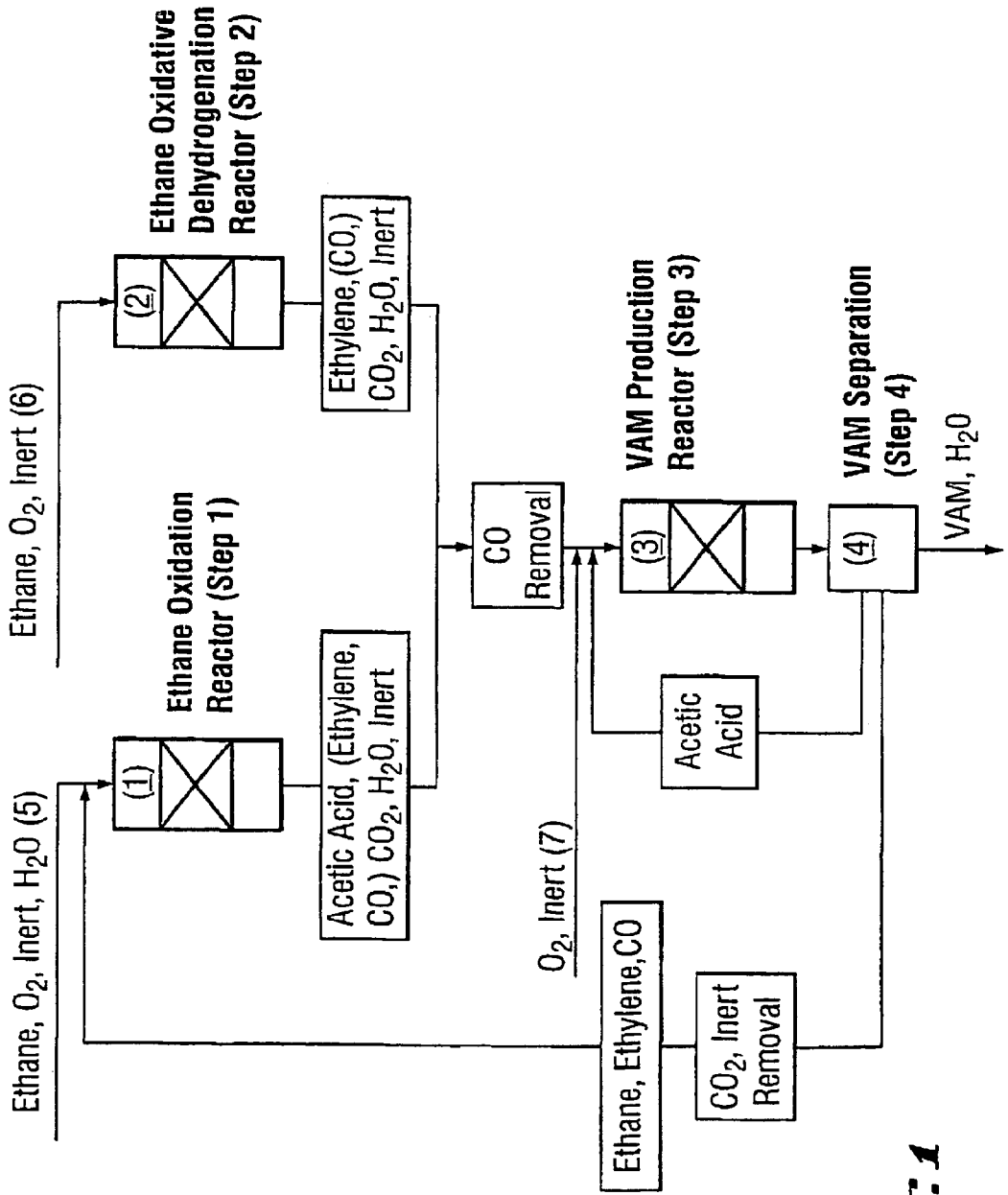

This application is a 371 of PCT/EP00/04545 filed May 19, 2000.

STATE OF THE ART

The present invention relates generally to an integrated process for the production of vinyl acetate and in particular to an integrated process for the production of vinyl acetate from a gaseous feedstock comprising essentially ethane.

Vinyl acetate is generally prepared commercially by contacting acetic acid and ethylene with molecular oxygen in the presence of a catalyst active for the production of vinyl acetate. Suitably, the catalyst may comprise palladium, an alkali metal acetate promoter and an optional co-promoter (for example, gold or cadmium) on a catalyst support. Acetic acid produced by carbonylation generally requires extensive purification to remove inter alia iodides arising from the catalyst system generally employed because iodides are recognised as potential vinyl acetate catalyst poisons.

Combinations of processes for producing vinyl acetate are known in the art. Thus, WO 98/105620 discloses a process for the production of vinyl acetate and/or acetic acid which process comprises first contacting ethylene and/or ethane with oxygen to produce a first product stream comprising acetic acid, water and ethylene, contacting in a second reaction zone in the presence or absence of additional ethylene and/or acetic acid the first product stream with oxygen to produce a second product stream comprising vinyl acetate, water, acetic acid and optionally ethylene; separating the product stream from the second step by distillation into an overhead azeotrope fraction comprising vinyl acetate and water and a base fraction comprising acetic acid; either recovering acetic acid from the base fraction and optionally recycling the azeotrope fraction or recovering vinyl acetate from the azeotrope fraction. The catalysts suggested in WO 98/05620 for the oxidation of ethylene to acetic acid or ethane to acidic acid are catalysts of the formula

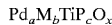

with M being selected from Cd, Au, Zn, Tl, alkali metals and alkaline earth metals; other catalysts for the oxidation of ethane to acetic acid are catalysts of the formula

with M being selected from Co, Cu, Re, Fe, Ni, Nb, Cr, W, U, Ta, Ti, Zr, Zn, Hf, Mn, Pt, Pd, Sn, Sb, Bi, Ce, As, Ag and Au or catalysts for the oxidation of ethane and/or ethylene to form ethylene and/or acetic acid which catalysts comprise the elements A, X and Y, wherein A is $Mo_dRe_eW_f$ and wherein X is Cr, Mn, Nb, Ta, V or W and wherein Y is Bi, Ce, Co, Cu, Fe, K, Mg, Ni, P, Pb, Sb, Si, Sn, Tl or U.

Other catalysts for the oxidation of ethane to acetic acid and ethylene suggested in WO 98/05620 are those of the formula

with Z being selected from Li, Na, Be, Mg, Ca, Sr, Ba, Zn, Cd, Hg, Sc, Y, La, Ce, Al, Tl, Ti, Zr, Hf, Pb, Nb, Ta, As, Sb, Bi, Cr, W, U, Te, Fe, Co, Ni.

U.S. Pat. No. 5,185,308 which is cited in WO 98/05620 describes examples wherein space time yields in the range between 555 and 993 g vinyl acetate per hour per liter catalyst are achieved.

OBJECTS OF THE INVENTION

It is an object of the present invention to provide for an integrated process for the production of vinyl acetate from a gaseous feedstock comprising essentially ethane as the only external carbon source of raw material supply, the process exhibiting space/time yields in the range of from 100 to 2000 grams of vinyl acetate per hour per liter of catalyst, preferably 500 to 1500 grams of vinyl acetate per hour per liter of catalyst.

THE INVENTION

Accordingly the present invention provides an integrated process for the production of vinyl acetate which comprises the steps:

1) contacting in a first reaction zone a gaseous feedstock comprising essentially ethane with a molecular oxygen-containing gas in the presence of a catalyst to produce a first product stream comprising acetic acid;
2) contacting in a second reaction zone a gaseous feedstock comprising essentially ethane with a molecular oxygen-cntaining gas in the presence of a catalyst to produce a second product stream comprising ethylene;
3) contacting in a third reaction zone in the presence or absence of additional ethylene or acetic acid the first gaseous product stream and the second gaseous product stream with a molecular oxygen-containing gas in the presence of a catalyst to produce a fourth product stream comprising vinyl acetate;
4) separating the product stream from step (3) and recovering vinyl acetate from said product stream from step (3).

The process according to the invention is based on the findings that a certain class of catalysts is capable of converting ethane to either acetic acid or ethylene with a very high selectivity and very high space time yield. Such separate ethylene and acetic acid product streams can than be mixed in the appropriate ratio and directly fed into a reactor to form vinyl acetate.

Using ethane instead of ethylene as feedstock has the advantage, that it is available in natural gas. In the process of natural gas work-up, several ethane-containing mixtures are obtained, which are usually simply flared off, but which all can be used as carbon feedstock for performing the process of the present invention.

Of specific advantage in the integrated vinyl acetate process of the present invention is that, in principal, infrastructures, utilities, and other features can be combined, for example only a single feed gas compressor and off-gas scrubbing system is required whereas separate acetic acid and vinyl acetate processes each require their own feed gas compressor and off-gas scrubbing system.

By combining steps 1, 2 and 3 of the present invention, reduced intermediate storage requirements are needed as compared to two separate processes. All these advantages lead to reduced capital and operating costs.

According to the invention a gaseous feedstock comprising essentially ethane is contacted in a first reaction zone with a molecular oxygen-containing gas in the presence of a catalyst active for the oxidation of ethane to acetic acid to produce a first product stream comprising acetic acid.

The catalyst active for the oxidation of ethane to acetic acid may comprise any suitable catalyst as described in DE-A 197 45 902 which is incorporated herein by reference. These catalysts are of the formula

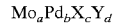

wherein X and Y have the following meaning:
X is selected from one or more elements of the group consisting of Cr, Mn, Nb, Ta, Ti, V, Te and W;
Y is selected from one or more elements of the group consisting of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Nb, Zr, Hf, Ni, P, Pb, Sb, Si, Sn, Tl and U and wherein a, b, c and are gram atom ratios and denote
a=1;
b=0.0001–0.01; preferably 0.0001–0.005
c=0.4–1; preferably 0.5–0.8 and
d=0.005–1; preferably 0.01–0.3.

Preferred catalysts are those wherein X is V and Y is Nb, Sb and Ca. Pd ratios above the indicated gram atom limit favor the formation of carbon dioxide; Pd ratios below the indicated gram atom limit favor the formation of ethylene and in consequence the formation of acetic acid. A catalyst specifically preferred for the process according to the invention is $Mo_{1.00}Pd_{0.00075}V_{0.55}Nb_{0.09}Sb_{0.01}Ca_{0.01}$.

In the second reaction zone—which is spatially separate from the first reaction zone—a gaseous feedstock comprising essentially ethane is contacted with a molecular oxygen-containing gas in the presence of a catalyst active for the oxidation of ethane to ethylene to produce a second product stream comprising ethylene.

The catalysts active for the oxidation of ethane to ethylene may comprise the same catalysts as disclosed above for the oxidation of ethane to acetic acid. Both processes differ in their reaction conditions, especially in the total pressure, residence time and water content in the feed. The oxidation of ethane to acetic acid is more favourable at higher total pressures compared to the oxidative dehydrogenation of ethane to ethylene. Acetic acid formation is the preferred reaction product when feeding steam together with ethane and the molecular oxygen containing gas, while steam can be facultatively used for the oxidative dehydrogenation of ethane to ethylene, but it is not absolutely necessary.

Preferred catalysts are those wherein X is V and Y is Nb, Sb and Ca. Pd ratios above the indicated gram atom limit favour the formation of carbon dioxide; Pd ratios below the indicated gram atom limit favour the formation of ethylene. A catalyst specifically preferred for the process according to the invention is $Mo_{1.00}Pd_{0.00075}V_{0.55}Nb_{0.09}Sb_{0.01}Ca_{0.01}$.

Useful catalysts for the oxidative dehydrogenation of ethane to ethylene can also be V—Al, V—Nb—Al, Cr—Nb—Al and Cr—Ta—Al based oxides which were shortly described (Liu, Y.; Cong, P.; Doolen, R. D.; Turner, H. W.; Weinberg, H.; Second Int. Symposium on Deactivation and Testing of Catalysts Presented Before the Division of Petroleum Chemistry, Inc.; $219^{th}$ National Meeting, ACS, San Francisco, Calif., Mar. 26–31, 2000; 298–302).

Moreover, several other patents describe more generally the oxidative dehydrogenation of paraffins. Three patents should be exemplary cited here which describe the oxidative dehydrogenation of paraffins on Ni oxide based catalysts. E. g., U.S. Pat. No. 4,751,342 describes the use of an alkali-doped Ni—P—Sn oxide catalyst, GB 2 050 188 describes Ni—Pb catalysts, and U.S. Pat. No. 3,886,090 describes Ni—Mg oxide catalysts which are modified with several other elements.

It is an advantage of the present invention that the ratio of selectivity to acetic acid to selectivity to ethylene which is formed in the first reaction zone can be varied within wide ranges, i.e. from 0 to 95% each by changing reaction parameters such as reaction temperature, total pressure, partial pressures of reactants, residence time, etc.

The reactions in the first and the second reaction zone preferably are carried out such that the amounts of acetic acid and ethylene formed in these reactions are in an appropriate ratio so that the combined first and second product stream can be directly fed into the third reaction zone to form vinyl acetate without the need to feed additional acetic acid or ethylene.

The catalysts active for the oxidation of ethane may be used supported or unsupported. Examples of suitable supports include silica, diatomaceous earth, montmorillonite, alumina, silica alumina, zirconia, titania, silicon carbide, activated carbon, and mixtures thereof. The catalyst active for the oxidation of ethane may be used in the form of a fixed or fluidised bed.

The molecular oxygen-containing gas used in all reaction zones may be air or a gas richer or poorer in molecular oxygen than air. A suitable gas may be, for example oxygen diluted with a suitable diluent, for example nitrogen or carbon dioxide. Preferably the molecular oxygen-containing gas is fed to the first and second reaction zone independently from the ethane feedstock.

The ethane feedstock of the process of the present invention may be substantially pure, or slightly diluted with other gases like the one beeing generated by natural gas separation, i.e. e.g. 90 Wt-% (PERP-report "Natural Gas Liquids Extraction 94/95 S4, P. 60") or may be admixtures with one or more of nitrogen, carbon dioxide, hydrogen, and low levels of C3/C4 alkenes/alkanes. Catalyst poisons like sulphur should be excluded. Likewise is it advantageous to minimise the amount of acetylene. The amount of inert components is only limited by economics.

Step (1) of the process of the present invention may suitably be carried out by passing ethane, the molecular oxygen-containing gas, steam and (if necessary) additional inerts through the catalyst. The amount of steam may suitably be in the range from 0 to 50 Vol %. The molar ratio of ethane to oxygen may suitably be in the range between 1:1 and 10:1, preferably between 2:1 and 8:1.

Step (1) of the process of the present invention may suitably be carried out at a temperature from 200 to 500° C., preferably from 200 to 400° C.

Step (1) of the process of the present invention may suitably be carried out at atmospheric or superatmospheric pressure, for example in the range from 1 to 100 bar, preferably from 1 to 50 bar.

Typically, ethane conversions in the range of 10 to 100%, especially 10 to 40% may be achieved in step (1) of the process of the present invention, depending on the reactor concept of step 1, which can also be a reactor cascade with interstitial oxygen feed.

Typically, oxygen conversions in the range 90 to 100% may be achieved in step (1) of the process of the present invention.

In step (1) of the process of the present invention, the catalyst suitably has a productivity ("space time yield" =STY) in the range 100 to 2000 grams of acetic acid per hour per liter of catalyst, preferably in the range 100 to 1500 grams of acetic acid per hour per liter of catalyst.

Step (1) of the present invention can be carried out in fixed bed as well as in fluidised bed reactors.

The gaseous product stream from step (1) comprises acetic acid and water, and may contain ethane, ethylene, oxygen, nitrogen and the by-products, carbon monoxide and carbon dioxide. Usually, no or very small amounts (<100 ppm) of carbon monoxide are produced in step (1). In case that carbon monoxide is produced in higher amounts up to 5%, it may—if necessary—be removed after step (1), e.g. by adsorption or by combustion to carbon dioxide by a molecular oxygen-containing gas. The acetic acid is present in the gaseous product stream of step (1) preferably in an amount as is required for direct conversion to vinyl acetate with the ethylene contained in the second product stream which will be combined with this first product stream.

Step (2) of the process of the present invention may suitably be carried out by passing ethane, the molecular oxygen-containing gas, steam and (if necessary) additional inerts through the catalyst. The amount of steam may suitably be in the range from 0 to 50 Vol %. The molar ratio of ethane to oxygen may suitably be in the range between 1:1 and 10:1, preferably between 2:1 and 8:1.

Step (2) of the process of the present invention may suitably be carried out at a temperature from 200 to 500° C., preferably from 200 to 400° C.

Step (2) of the process of the present invention may suitably be carried out at atmospheric or superatmospheric pressure, for example in the range from 1 to 50 bar, preferably from 1 to 30 bar.

Typically, ethane conversions in the range of 10 to 100%, especially 10 to 40% may be achieved in step (2) of the process of the present invention, depending on the reactor concept of step (2), which can also be a reactor cascade with interstitial oxygen feed.

Typically, oxygen conversions in the range 90 to 100% may be achieved in step (2) of the process of the present invention.

In step (2) of the process of the present invention, the catalyst suitably has a productivity (STY) in the range 100 to 2000 grams of ethylene per hour per liter of catalyst, preferably in the range 100 to 1500 grams of ethylene per hour per liter of catalyst.

Step (2) of the present invention can be carried out in fixed bed as well as in fluidised bed reactors.

The gaseous product stream from step (2) comprises ethylene and water, and may contain ethane, acidic acid, oxygen, nitrogen and the by-products, carbon monoxide and carbon dioxide. Usually, no or very small amounts (<100 ppm) of carbon monoxide are produced in step (2). In case that carbon monoxide is produced in higher amounts up to 5%, it may—if necessary—be removed after step (2), e.g. by adsorption or by combustion to carbon dioxide by a molecular oxygen-containing gas. The ethylene is present in the gaseous product stream of step (2) preferably in an amount as is required for direct conversion to vinyl acetate with the acidic acid contained in the first product stream which will be combined with this second product stream.

The ethylene/acidic acid ratio which is necessary for feeding the vinyl acetate reactor (step (3)) of the present invention may suitably be adjusted by changing the reaction parameters of step (1) and/or step (2), e.g. reaction temperature, total pressure, gaseous hourly space velocity, partial pressures of each reactant and, especially, by varying the steam partial pressure in the feed of step (1).

The gaseous product from step (1) and the gaseous product from step (2) may be fed directly to the third reaction zone of step (3) together with optionally additional molecular oxygen-containing gas, optionally additional ethylene and optionally additional acetic acid, which can preferably be taken from step (4), the vinyl acetate separation.

The catalyst active for the production of vinyl acetate which is used in step (3) of the process of the present invention may comprise any suitable catalyst known in the art, for example, as described in GB 1 559 540, U.S. Pat. No. 5,185,308 and WO 99/08791.

EP-A 0 330 853 describes catalysts for the production of vinyl acetate all-throughout impregnated containing Pd, K, Mn and Cd as additional promotor instead of Au.

GB 1 559 540 describes a catalyst active for the preparation of vinyl acetate by the reaction of ethylene, acetic acid and oxygen, the catalyst consisting essentially of:
(1) a catalyst support having a particle diameter of from 3 to 7 mm and a pore volume of from 0.2 to 1.5 ml/g, a 10% by weight water suspension of the catalyst support having a pH from 3.0 to 9.0, (2) a palladium-gold alloy distributed in a surface layer of the catalyst support, the surface layer extending less than 0.5 mm from the surface of the support, the palladium in the alloy being present in an amount of from 1.5 to 5.0 grams per liter of catalyst, and the gold being present in an amount of from 0.5 to 2.25 grams per liter of catalyst, and (3) from 5 to 60 grams per liter of catalyst of alkali metal acetate.

U.S. Pat. No. 5,185,308 describes a shell impregnated catalyst active for the production of vinyl acetate from ethylene, acetic acid and an oxygen containing gas, the catalyst consisting essentially of
(1) a catalyst support having a particle diameter from about 3 to about 7 mm and a pore volume of 0.2 to 1.5 ml per gram,
(2) palladium and gold distributed in the outermost 1.0 mm thick layer of the catalyst support particles, and
(3) from about 3.5 to about 9.5% by weight of potassium acetate wherein the gold to palladium weight ratio in said catalyst is in the range 0.6 to 1.25.

WO 99/08791 describes a method for producing catalysts containing metal nanoparticles on a porous support, especially for gas phase oxidation of ethylene and acetic acid to form vinyl acetate. The invention relates to a method for producing a catalyst containing one or several metals from the group of metals comprising the sub-groups Ib and VIIIb of the periodic table on porous support particles, characterised by a first step in which one or several precursors from the group of compounds of metals from sub-groups Ib and VIIIb of the periodic table is or are applied to a porous support, and a second step in which the porous, preferably nanoporous support to which at least one precursor has been applied is treated with at least one reduction agent, to obtain the metal nanoparticles produced in situ in the pores of said support.

Typically, step (3) of the process of the present invention is carried out heterogeneously with the reactants being present in the gas phase.

The molecular oxygen-containing gas used in step (3) of the process of the present invention may comprise unreacted molecular oxygen-containing gas from step (1) or (2) and/or additional molecular oxygen-containing gas. Preferably, at least some of the molecular oxygen-containing gas is fed independently to the third reaction zone from the acetic acid and ethylene reactants.

Step (3) of the process of the present invention may suitably be carried out at a temperature in the range from 140 to 220° C.

Step (3) of the process of the present invention may suitably be carried out at a pressure in the range from 1 to 100 bar.

Step (3) can be carried out in any suitable reactor design capable of removing the heat of reaction in an appropriate way; preferred technical solutions are fixed or fluidised bed reactors.

Acetic acid conversions in the range 5 to 50% may be achieved in step (3) of the process of the present invention.

Oxygen conversions in the range 20 to 100% may be achieved in step (3) of the present invention.

In step (3) of the process of the present invention, the catalyst suitably has a productivity (STY) in the range 100 to 2000 grams of vinyl acetate per hour per liter of catalyst, but >10000 grams of vinyl acetate per hour per liter of catalyst is also suitable.

The third product stream from step (3) of the process comprises vinyl acetate and water and optionally also unreacted acetic acid, ethylene ethane, nitrogen, carbon monoxide, carbon dioxide and possibly present traces of other byproducts. Intermediate between step (3) and step (4) of the process of the invention it is preferred to remove ethylene, and ethane, carbon monoxide and carbon dioxide, if any, from the third product stream, suitably as an overhead gaseous fraction from a scrubbing column, in which a liquid fraction comprising vinyl acetate, water and acetic acid is removed from the base.

The third product stream from step (3) comprising vinyl acetate, water and acetic acid, with or without the intermediate scrubbing step, is separated in step (4) by distillation into an overhead azeotrope fraction comprising vinyl acetate and water and a base fraction comprising acetic acid.

Vinyl acetate is recovered from the azeotrope fraction separated in step (3), suitably for example by decantation. The recovered vinyl acetate may, if desired, be further purified in known manner. The base fraction comprising acetic acid separated in step (3) is preferably recycled, with or preferably without further purification, to step (3) of the process.

The overall Space Time Yield (STY) of vinyl acetate (referred to ethane) produced in the process is in the range of 100 to 5000, preferably in the range of 500 to 1500 grams of vinyl acetate per hour per liter of catalyst.

The overall yield may be adjusted in a number of ways including independently adjusting the reactant ratios and/or reaction conditions of step (1) and/or step (2) and/or step (3) of the process, for example by independently adjusting the oxygen concentration(s) and/or the reaction temperatures and pressures.

The process of the present invention will now be illustrated by example with reference to FIG. 1 which represents in schematic form apparatus for use in the process of the present invention.

The apparatus comprises a first reaction zone (1), a second reaction zone (2), a third reaction zone (3) and a scrubber column (4).

In use, a molecular oxygen-containing gas, optional steam and a gaseous feedstock comprising essentially ethane (5) are fed to the first reaction zone (1) which contains a catalyst active for the oxidation of ethane to form acetic acid. Depending on the scale of the process, the first reaction zone (1) may comprise either a single reactor or several reactors in parallel or series. The first reaction zone may also comprise a reactor cascade, wherein between the individual reactors additional molecular oxygen-containing gas can be fed. A first gaseous product stream comprising acetic acid, unreacted feedstock, optionally unconsumed molecular oxygen-containing gas and water together with carbon monoxide, carbon dioxide, and inerts is withdrawn from the first reaction zone (1).

The second reaction zone (2) is fed with a molecular oxygen-containing gas, optional steam and a gaseous feedstock comprising essentially ethane (6). The reaction zone (2) contains a catalyst active for the oxidation of ethane to form ethylene. Depending on the scale of the process, the second reaction zone (2) may comprise either a single reactor or several reactors in parallel or series. The second reaction zone may also comprise a reactor cascade, wherein between the individual reactors additional molecular oxygen-containing gas can be fed. A second gaseous product steam comprising ethylene, unreacted feedstock, optionally unconsumed molecular oxygen-containing gas and water together with carbon monoxide, carbon dioxide, and inerts is withdrawn from the second reaction zone (2).

The first and the second product stream are fed to the third reaction zone (3). Additional molecular oxygen-containing gas (7) may be mixed with the product stream withdrawn from the first and the second reaction zone (1) and (2). In the third reaction zone (3) acetic acid and ethylene are contacted with molecular oxygen-containing gas in the presence of a catalyst active for the production of vinyl acetate. Depending on the scale of the process, the third reaction zone (3) may comprise either a single reactor or several reactors in parallel or in series. A product stream comprising vinyl acetate, water, optionally ethane, gaseous by-products and unreacted acetic acid and ethylene is withdrawn from the third reaction zone (3) and is fed to the scrubber column (4) where a gaseous stream comprising ethylene, and optionally ethane together with inerts, carbon monoxide and carbon dioxide by-products is withdrawn overhead and is recycled to the first or second reaction zone (1)/(2). A liquid stream comprising vinyl acetate, water, unreacted acetic acid and possibly present other high boiling products of the process are withdrawn from the base of the scrubber column (4) and vinyl acetate is isolated in state of the art equipment not shown. For example it is fed to a distillation column where vinyl acetate and water is removed as an azeotrope and acetic acid, and possibly present other high boiling products are removed as a bleed from the base of the distillation column. The water in the overhead stream from the distillation column can be separated from the vinyl acetate in a decanter and a vinyl acetate product stream removed from decanter is purified by conventional means known in the art.

Carbon dioxide by-product can be removed by any viable technical process known in the art e.g. by reversible absorption in an aqueous $K_2CO_3$ solution which is regenerated in a desorption column (not shown).

The invention is illustrated in the following examples.

EXAMPLES

Preparation of Catalysts

Example (1)

Preparation of catalyst I: $Mo_{1.00}Pd_{0.00075}V_{0.55}Nb_{0.09}Sb_{0.01}Ca_{0.01}O_x$ Solution 1 80 g ammonium molybdate (Riedel-de Haen) in 400 ml water.

Solution 2 29.4 g ammonium metavanadate (Riedel-de Haen) in 400 ml water.

Solution 3 19.01 g niobium ammonium oxalate (H. C. Starck), 1.92 g antimony oxalate (Pfaltz & Bauer), and 1.34 g calcium nitrate (Riedel-de Haen) in 200 ml water.

Solution 4 0.078 g palladium(II)acetate (Aldrich) in 200 ml ethanol.

Solutions 1, 2 and 3 were stirred separately at 70° C. for 15 minutes. Then, solution 3 was poured into solution 2, and stirred together at 70° C. for another 15 minutes before adding this into solution 1. Thereafter, solution 4 was added.

The resulting mixture was evaporated to obtain a remaining total volume of 800 ml. This mixture was spray-dried at 180° C. followed by drying the powder in static air at 120° C. for 2 hours and calcining at 300° C. for 5 hours.

Example (2)

Preparation of catalyst II: $K,Pd,Au/TiO_2$ 2.11 g palladium acetate (Aldrich) and 1.32 g gold acetate were dissolved in 30 ml acetic acid. The preparation of the employed gold acetate is described e.g. in U.S. Pat. No. 4,933,204. 100 ml $TiO_2$ support (P25 pellets, Degussa, Hanau) were added to the palladium and gold acetate solution. Then, the majority of acetic acid was evaporated using a rotary evaporator at 70° C., followed by evaporating the rest using an oil pump at 60° C. and finally in a vacuum drying cabinet at 60° C. for 14 h.

The resulting pellets were reduced with a gas mixture of 10 Vol % hydrogen in nitrogen, while passing the gas (40 l/h) directly through the pellets at 500° C. and 1 bar for 1 h. For loading with potassium ions, the reduced pellets were added to a solution containing 4 g potassium acetate in 30 ml of water, for 15 minutes in a mixing apparatus.

Then, the solvent was evaporated using a rotary evaporator. The pellets were dried at 100° C. for 14 h.

Catalyst II was prepared in three batches using the same process; they are called II a, II b and II c, respectively.

All catalysts were then pressed, broken and sieved into a granular fraction between 0.35 and 0.70 mm for performing the catalytic tests.

Catalytic Tests

For performing the catalytic reaction described in steps (1), (2) and (3) of the present invention, double-wall fixed bed reactors with an inner diameter of 14 mm and 20 mm, respectively, and a length of 350 mm were used. The reactor was heated via the external tube with an oil bath. Typically, 5 ml and 15 ml of catalyst, respectively, partially mixed with some inert material, e.g. typically glass, quartz or alumina granules or beads in a catalyst to inert material volume ratio of e.g. 2:1, 1:1, 1:2, 1:5. To decrease the dead volume of the reactor, it was filled up with inert material (as mentioned above) before and after the catalyst bed. The volume flows were typically adjusted by mass and liquid flow controllers, respectively.

The analysis of reaction products was performed by on-line gas chromatography.

The results of catalytic measurements on catalysts I to XIII (examples (1 to 13)) for performing steps (1) and (2) of the present invention using one single reactor are shown in Tables 1 and 2. Measurements of step (1) (results presented in Table 1) were performed at 15 bar.

Data in Tables 1 and 2 are defined as follows:

Conversion of ethane $[\%]=(0.5*[CO]+0.5*[CO_2]+[C_2H_4]+[CH_3COOH])/(0.5*[CO]+0.5*[CO_2]+[C_2H_4]+[C_2H_6]+[CH_3COOH])*100$ Selectivity to ethylene $[\%]=([C_2H_4])/(0.5*[CO]+0.5*[CO_2]+[C_2H_4]+[CH_3COOH]*100$ Selectivity to acetic acid $[\%]=([CH_3COOH])/(0.5*[CO]+0.5*[CO_2]+[C_2H_4]+[CH_3COOH])*100$ with

[ ]=concentration in mol %

$[C_2H_6]$=concentration of ethane not converted $\tau[s]$=catalyst volume (ml)/volume flow of the gas (ml/s) at reaction conditions STY=g product/(l catalyst*h)

Catalyst II (example (2)) was used in step (3) of the present invention for the production of vinyl/acetate. The catalytic test was performed at reaction temperatures in the range from 150 to 170° C., at reaction pressures from 8 to 9 bar.

The results of catalytic measurements on catalyst II (example (2)) for performing step (3) of the present invention are shown in Table 2.

Data in Table 2 are defined as follows;

Selectivity to vinyl acetate (VAM) $[\%]=([VAM])/([VAM]+0.5*[CO]+0.5*[CO_2])*100$ with

[ ]=concentration in mol %

STY=g product/(l catalyst*h)

TABLE 2

Catalytic results on catalyst II performing the vinyl acetate synthesis

| | Reaction Conditions | | Results | |
|---|---|---|---|---|
| | | | Selectivity | Space Time Yield |
| No. | T [°C] | P [bar] | S (VAM) [%] | STY [g/(h)] |
| a | 155 | 9 | 98 | 1000 |
| a | 160 | 9 | 98 | 1050 |
| a | 170 | 9 | 96 | 1000 |
| b | 160 | 9 | 98 | 1150 |
| b | 170 | 9 | 97 | 700 |
| c | 170 | 9 | 98 | 1300 |

What is claimed is:

1. An integrated process for the production of vinyl acetate which comprises the steps of:
   1) contacting in a first reaction zone a gaseous feedstock comprising mainly ethane with a molecular oxygen-containing gas in the presence of a catalyst to produce a gaseous product stream comprising acetic acid;
   2) contacting in a second reaction zone a gaseous feedstock comprising mainly ethane with a molecular oxygen-containing gas in the presence of a catalyst to produce a second gaseous product stream comprising ethylene;
   3) contacting in a third reaction zone the first gaseous product stream and the second gaseous product stream with a molecular oxygen-containing gas in the presence of a catalyst to produce a fourth product stream comprising vinyl acetate;

TABLE 1

Catalytic results on catalyst I performing the ethane oxidation to acetic acid

| | Reaction Conditions | | | | | | | Results | | | |
|---|---|---|---|---|---|---|---|---|---|---|---|
| | | | Feed Composition | | | | Conversion | S | S | S | Space Time Yield STY |
| Run No. | T [°C.] | t [s] | V($C_2H_5$) [ml/s] | V($O_2$) [ml/s] | V($N_2$) [ml/s] | V($H_2O$) [ml/h] | X($C_2H_5$) [%] | (HOAc) [%] | ($C_2H_4$) [%] | (CO + $CO_2$) [%] | (HOAc) [g/(h)] |
| 1 | 280 | 14.8 | 1.0 | 0.2 | 0.8 | 1.4 | 13.3 | 91.5 | 0.7 | 7.8 | 235 |
| 2 | 280 | 7.4 | 2.0 | 0.4 | 1.6 | 2.9 | 10.5 | 90.4 | 3.5 | 6.0 | 362 |
| 3 | 300 | 7.1 | 2.0 | 0.4 | 1.6 | 2.9 | 13.2 | 89.0 | 2.0 | 9.0 | 447 |
| 4 | 300 | 4.8 | 3.0 | 0.6 | 2.4 | 4.3 | 11.3 | 87.2 | 5.5 | 7.3 | 564 |
| 5 | 300 | 4.1 | 3.5 | 0.7 | 2.8 | 5.0 | 10.2 | 86.2 | 7.4 | 6.4 | 584 |
| 6 | 300 | 3.7 | 4.0 | 0.8 | 3.2 | 5.0 | 9.9 | 84.1 | 9.2 | 6.6 | 630 |

4) separating the product stream from step (3) and recovering vinyl acetate from said product stream from step (3) wherein the catalyst in the first and second reaction zone is of the formula

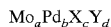
$Mo_aPd_bX_cY_d$ wherein X and Y have the following meaning:
X is at least one element selected from the group consisting of Cr, Mn, Nb, Ta, Ti, V, Te and W:
Y is at least one element selected from the group consisting of B, Al, Ga, In, Pt, Zn, Cd, Bi, Ce, Co, Rh, Ir, Cu, Ag, Au, Fe, Ru, Os, K, Cs, Mg, Ca, Sr, Ba, Nb, Zr, Hf, Ni, P, Pb, Sb, Si, Sn, Tl and U and wherein a, b, and c are gram atom ratios and denote
a=1;
b=0.000–0.1;
c=0.1–1;
d=0.005–1.

2. The process according to claim 1 wherein gaseous feedstock for step (1) comprises ethane, molecular oxygen-containing with an ethane to oxygen ratio in the range between 1:1 and 10:1 and 0 to 50 Vol-% steam (based on the total volume of the gaseous feedstock).

3. The process according to claim 1 wherein the gaseous feedstock for step (2) comprises ethane, molecular oxygen-containing gas with an ethane to oxygen ratio in the range between 1:1 and 10:1.

4. The process according claim 1 wherein additional ethylene and/or acetic acid from recycle gas is fed to the third reaction zone.

5. The process according to claim 1 wherein the molecular oxygen-containing gas is fed to the first and/or second reaction zone independently from the ethane feedstock.

6. The process according to claim 1 wherein the molecular oxygen-containing gas is fed independently to the third reaction zone from the acetic acid and ethylene reactants.

7. The process of claim 1 wherein b is 0.0001 to 0.0005, c is 0.5 to 0.8 and d is 0.01 to 0.3.

* * * * *